(12) United States Patent
Ramachandraiah et al.

(10) Patent No.: US 6,365,786 B1
(45) Date of Patent: Apr. 2, 2002

(54) ECO-FRIENDLY METHOD OF PREPARATION OF HIGH PURITY TETRABROMOBISPHENOL-A

(75) Inventors: Gadde Ramachandraiah; Pushpito Kumar Ghosh; Aditya Shantilal Mehta; Rajesh Popatlal Pandya; Ashok Dahyabhai Jethva; Sanjay Shambhubhai Vaghela; Sudhindra Nath Misra, all of Gujarat (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/767,667

(22) Filed: Jan. 22, 2001

(51) Int. Cl.$^7$ ................................................ C07C 39/16
(52) U.S. Cl. ...................................................... 568/726
(58) Field of Search ......................................... 568/726

(56) References Cited

U.S. PATENT DOCUMENTS 3,546,302 A * 12/1970 Asadorian
3,929,907 A * 12/1975 Janzon
4,112,242 A * 9/1978 Swietoslawski
4,180,684 A * 12/1979 Kleinschmit

* cited by examiner

Primary Examiner—Michael L. Shippen
(74) Attorney, Agent, or Firm—Abelman, Frayne & Schwab

(57) ABSTRACT

A highly pure and colorless tetrabromobisphenol-A (TBBPA) possessing melting point in the range of 178–182° C. is prepared in yields of 50–70% in first batch and 90–100% when the spent organic layer is recycled. In this method, the corrosive liquid bromine is displaced by sodium bromide/hydrobromic acid as brominating agent. Further, sodium bromate is used as an oxidizing as well as brominating agent to utilize the hydrobromic acid that is produced during the bromination of bisphenol-A (BPA). The reaction is conducted at 10–15° C. in a mixture of methylene chloride-water or carbon tetrachloride-water in the presence of hydrochloric acid and sodium lauryl sulfate. The crystalline product settled at the bottom of the reaction vessel is filtered, washed, dried and weighed. The spent organic layer is recycled in subsequent batches to maximize the overall yield of product recovered directly as solid and to minimize generation of organic effluent.

15 Claims, No Drawings

ECO-FRIENDLY METHOD OF PREPARATION OF HIGH PURITY TETRABROMOBISPHENOL-A

FIELD OF THE INVENTION

The present invention relates to an eco-friendly method of preparation of high purity tetrabromobisphenol-A.

BACKGROUND OF THE INVENTION

Tetrabromobisphenol-A, $(CH_3)_2C(C_6H_2Br_2OH)_2$ (TBBPA, 79-94-7) is an -important substance among various bromo compounds. It is a bromo derivative of bisphenol-A (BPA). It is used as a flame retardant with over one-third of the total brominated flame-retardant because of high stability and suitability as an additive and reactive compound. TBBPA is also used in the preparation of acrylonitrile butadiene styrene (ABS) polymer as well as in the preparations of epoxy and polycarbonate resins. These resins in turn are widely used for the manufacture of electronic equipment, in particular of computer-printed circuit boards. The resins are also used as fire retardant in the manufacture of coatings, plastics, paints, adhesives and laminates as the high level activity of TBBPA allows it to be used at relatively low loading, translating to a greater retention of the physical properties of the base polymer.

BACKGROUND OF THE INVENTION

Reference may be made to K. Matsuda, M. Sugino and S. Kaji Japan, Kokai 74,108,003, Cl. 16 B21, Oct. 14, 1974 wherein TBBPA was prepared by reacting liquid bromine with BPA in methanol over three hours at 10–30° C. The solution was then kept at 44–45° C. for 3 h, treated with 383 ml of 98% $H_2SO_4$ over 40 min at 20° C. and cooled to obtain the product. Nitrogen was-bubbled throughout to separate the by-product methyl bromide. The drawback is that it uses liquid bromine as brominating agent. Liquid bromine is a highly corrosive fuming liquid and air pollutant. Hence, it requires special equipment for its transport or storing and it needs safety measures. Thus, the method is convenient only to the bromine manufacturers. Besides these difficulties, only half of the total bromine used is utilized in the formation of product and the rest ends up as hydrobromic acid and methyl bromide as side products with the consumption of solvent which adversely affects the economics and also increases the number of unit operations. Moreover, the addition of concentrated sulfuric acid to the reaction vessel is hazardous as it is corrosive and liberates enormous heat due to dilution. Additionally, a cooling mechanism is required to absorb the heat evolved in the system, which unnecessarily enhances the product cost.

M. Ichimura, T. Nishiyama and K. Suzuki Japan Kokai 7654538, Cl. C07C25/18, May 13, 1976 prepared a high purity and less colored TBBPA by adding liquid bromine (43.68 Kg) to BPA (15.22 Kg) in tetra chloro ethylene (48 Kg) containing 0.2–1 times its weight water (66.7 Kg) at ≦40° C. over 1 h under stirring. About 99.1% TBBPA (36 Kg) was reported obtained on heating the mixture to ≧92° C. for 2 h with 99.6% purity. The drawback is that the liquid bromine requires special equipment to store or transport and safety measures as it is highly corrosive fuming liquid besides air pollutant. Also, it liberates hydrobromic acid as side product, which is not desired and has to be recycled with some more additional unit operations. Moreover, the heating of the reaction mixture to ≧92° C. for 2 h is energy intensive and thus increases the production cost.

D. R. Brackenridge U.S. Pat. No. 4,013,728, Cl. 260619A; C07 C37/00, Mar. 22, 1977 reported the preparation of TBBPA by adding the liquid bromine into BPA in 75–95% (w/w) aqueous acetic acid at 0–30° C. followed by heating to 80–120° C. for 5 to 60 min to give 92.3% product melting at 180–182° C. The drawbacks of this method are that both the liquid bromine and the solvent acetic acid are toxic and are air pollutants. The heating step after the addition of liquid bromine enhances the production cost. Additionally, hydrobromic acid is obtained as the byproduct, which has to be recovered from the solvent, and processed for its further use.

H. Jenkner and R. Strang Ger. Offen. 2,613,969, Cl. C07 C39/24, Oct. 6, 1977 reported a procedure for obtaining TBBPA. According to them, to a suspension of 171 parts by weight of BPA in 300 parts by volume of 1,1-dibromo ethane and 300 parts by volume of an aqueous solution containing 80 parts by weight of sodium bromate and 53 parts by weight of sodium bromide, liquid bromine (245 parts by weight) was added over 3 h at 28° C. under stirring to give 269 g TBBPA from the organic phase. The aqueous phase was restored to its original composition via an electrolytic process. The mother liquor from the initial preparation was added and the process was repeated without the need of an additional 1,1-dibromo ethane to give a total yield of 97% TBBPA. The drawback is that it uses 2 equivalents of liquid bromine, 1 equivalent of sodium bromide and 0.47 equivalents of sodium bromate as brominating agent. About 1.5 equivalents of bromine in the form of sodium bromide or hydrobromic acid remained unused in the reaction. Additionally this method requires an electrolytic treatment to the aqueous layer to restore to its original composition for reuse in the succeeding batches and requires special equipment and safety measures to store and transport the liquid bromine.

J. Swietoslawski, A. Silowiecki, A. Ratajczak, B. Nocon and Z. Baniak Ger. Offen. 2,718,997, Cl. C07 C39/24, Nov. 17, 1977 reported the preparation of TBBPA wherein 100 g of liquid bromine was added to a solution of 68.4 g BPA in 125 ml of methanol containing 11.1 ml of concentrated sulfuric acid over 30 min at 30–35° C. followed by 86 ml of 50% aqueous sodium chlorate over 45 min at 35–40° C. The solution is stirred for 2 h at 40–45° C. and cooled to 15° C. to obtain 148 g of TBBPA in 97% yield. The main drawbacks with this method are that both the liquid bromine and sodium chlorate are highly corrosive. Liquid bromine requires special equipment and safety measures to stop the air pollution and to avoid accidents. The use of non-bromo compound as an oxidizing agent to utilize the byproduct is an energy intensive step and it releases unwanted side product and further complicates the purification step.

W. Baumann, A. Block, I. Boehnke, J. Fiernow, H. Fischer, P. Franke E. Heynisch, D. Timm and H. Weber Ger. East DD 159,066, Cl. C07 C39/367, Feb. 16, 1983 and Ger East DD 211,781, Cl. C07 C39/367, Jul. 25, 1984 prepared TBBPA by the bromination of BPA with bromine liquid in methylene chloride and water medium. In this method, the organic layer was separated from the mother liquor and treated with 10% aqueous sodium hydroxide (Ger. East DD 159,066, Cl. C07 C39/367, Feb. 16, 1983) and distilled (Ger East DD 211,781, Cl. C07 C39/367, Jul. 25, 1984) to get solvent for the reuse. The drawback is that the handling of liquid bromine is hazardous as it is highly corrosive and air pollutant and also 50% of total bromine used is converted into hydrobromic acid, which increases the process steps and thus effects, the cost of production. The neutralization of hydrobromic acid existing in the organic layer with 10% sodium hydroxide and the electrolytic treatment of the aqueous layer for the reuse in succeeding batches are extra steps involved in addition to the problems associated with the corrosive liquid bromine.

I. Bohenke, U. Geyer and D. Timm German East DD 211,782, Cl. C07 C39/367, Jul. 25, 1984 brominated 175 g of BPA with 462 g of bromine in a mixture of 100 ml toluene, 200 ml methylene chloride and 600 ml water under stirring at 43° C. Methylene chloride (198 ml) was distilled and the product (398.5 g, m. p. 153–161° C.) was filtered from the remaining at 10° C. Apart from the use of liquid bromine, only 79.3% of TBBPA was obtained along with the products like di- (3.6%) and tri-bromo (17.1%) derivatives. The drawback is that it uses liquid bromine, which is corrosive and air pollutant and requires special equipment for storing and transporting. Hydrobromic acid is produced as an undesired byproduct by the consumption of 50% of the total bromine used in the operation and needs additional unit operations to recycle. Besides these problems, the yield of TBBPA is only 85% and is contaminated with di- (3.6%) and tri-bromo (17.1%) derivatives of bisphenol-A. Moreover, the filtration of the product at low temperatures requires special arrangements, which adds to the total cost of TBBPA.

U. Geyer, D. Timm and I. Boehnke Ger. East DD 808,344, Cl. C07 C39/367, May 2, 1984 brominated 175 g BPA with 458 g of bromine in (150 g) cyclohexane and (150 g) methylene chloride and (400 ml) water. A mixture of 0.3% mono-, 5%. di- and 18% tri-bromo derivatives along with 76.7% TBBPA was reported produced. The drawback with this technique is that it uses liquid bromine as brominating agent, which is corrosive and requires special equipment and safety devices. Half of the total bromine used in this method is converted to the undesired hydrobromic acid, which requires additional unit operations for recycling and thus affects the cost of TBBPA largely. Moreover, the intermediate products such as mono-, di-, and tri-bromo bisphenol-A whose separation from TBBPA is a difficult process. This method requires two organic solvents cyclohexane and methylene chloride.

I. Israeli IL 64,410, Cl. C07 C39/367, Mar. 31, 1985 obtained a highly pure TBBPA by the bromination of 320 g BPA with the addition of 465 g bromine liquid, 60 ml water, 2 g of 8% dodecylbenzene sulfonate, 185 g of 40% aqueous hydrogen peroxide and 750 ml of methylene chloride saturated with TBBPA. The drawback with this technique is that it uses liquid bromine as brominating agent, which is corrosive and requires special equipment and safety devices. Hydrogen peroxide used, as an oxidizing agent is a non-bromo compound and it disproportionate at room temperature to oxygen and water spontaneously. Thus, more than the stoichiometric amount of hydrogen peroxide is to be added at every batch. Ultimately, this enhances the cost of TBBPA production.

T. Ogata M. Aritomi and C. Asano Japan Tokyo Tokyo Koho JP 62,221,645; Cl. C07 C39/367, Sep. 29, 1987 reported the procedure for the preparation of TBBPA wherein liquid bromine was added drop wise to a dispersion of BPA in water-carbon tetrachloride at 15–18° C. over 1.5 h to get 99.2% TBBPA after heating to 70–72° C. for 2 h. The drawback with this technique is that it uses liquid bromine which is corrosive and toxic and it requires special equipment and safety devices. Half of the total bromine used in this method is converted to hydrobromic acid, which increases some more unit operations. Heating the reactants to 70–72° C. after the bromine addition is enhances the production cost.

C. Asano Japan Kokai Tokyo Koho JP 63,316,74, Cl. C07 C39/367, Dec. 26, 1988 obtained 99.2% pure TBBPA in a multi-stage reaction. According to him the addition of 142 g bromine over 2 h to a 50 g of BPA in 175 g chloro benzene and 125 g water at 15–20° C. gives 117.9 g of crystalline TBBPA containing 4 ppm bromide after heating the mixture at 15–20° C. for 1.5 h, stirring the mixture for 30 min at 80° C., adding 0.6 g of 60% hydrazine hydrate, heating to 90° C., separating the aqueous phase, washing the organic phase, depressing the organic phase to remove 62 g chloro benzene, and cooling the organic phase to 25° C. The drawbacks are that it requires corrosive liquid bromine for the bromination reaction and also hydrazine hydrate to reduce the impurities. The step heating to 80 and 90° C. adds to the cost of TBBPA. Further, this method liberates hydrobromic acid as the side product, which requires additional unit operation for reuse.

R. P. Pandya, M. M. Pandya, J. K. Langalia, P. R. Mehta and M. M. Taqui Khan Indian IV 162,522, Cl. C07 C27/00, Jun. 4, 1988 obtained 5 Kg of TBBPA (mp 181° C.) by adding 8.842 Kg of liquid bromine under stirring at ≦40° C. to 3 Kg of BPA dissolved in 3.5 l of ethyl alcohol and 1.4 l of water containing 1 g of ferric chloride as a catalyst. The drawbacks of this method are that it uses corrosive liquid bromine as brominating agent and losses 50% bromine in the formation of hydrobromic acid which requires additional unit operations to reuse. Moreover, the contents have to be stored for 24 h after the completion of the bromine addition, which brings down the production rate. On the other hand, the contents have to be diluted with large volume of water to recover maximum quantity of TBBPA. As a result, the process of separation of hydrobromic acid and recovery of alcohol from the mother liquor become difficult. Further, the catalyst iron adds, as impurity to the final product and thus it is difficult to get polycarbonate grade product by this method.

E. Walter Ger. Offen. DE, 3,935,224, Cl. C07 C39/367, Apr. 25, 1991 claimed the formation of TBBPA in the bromination of BPA with liquid bromine, hydrobromite /hydrogen bromide in an organic solvent like chloro benzene. 50% of aqueous hydrogen peroxide was added additionally whereby the hydrobromic acid produced during the reaction was oxidized to bromine. The TBBPA thus formed was heated to dissolve in the organic phase which was separated and washed with 1 M aqueous sodium sulfite and twice with water at 80° C. The drawback of this method is that the brominating agent is liquid bromine. Moreover, it requires hydrogen peroxide, which decomposes spontaneously at room temperature. The purification of TBBPA with aqueous sodium sulfite and water at 80° C. would add to the cost.

H. Eguchi, M. Kubo N. Nagasaki and K. Kunimoto Eur. Pat. 472,395, Cl. C07 C37/62, Feb. 26, 1992 patented the process of preparation of TBBPA wherein (58.8 g) BPA was brominated with (163 g) liquid bromine in (300 g) methanol. Additionally, they added 40.6 g of 36% hydrochloric acid to yield 96.5% product with 98.7% purity. The drawback is that it uses liquid bromine as a brominating agent, which requires special equipment and safety devices. In addition, the mother liquor obtained after the separation of product is highly acidic due to hydrochloric acid which has to be destroyed for its safe discharge. The undesired byproducts methyl bromide (0.3 g) and hydrobromic acid consume more than 50% bromine used, thereby reducing the bromine atom efficiency. B.G. Mckinnie, G. L. Sharp and R. E. William U.S. Pat. No. 5,283,375, Cl. 568–726 C07 C39/387, Feb. 1, 1994 prepared the TBBPA by adding 3.9–4.2 moles of bromine to 1 mole of BPA dissolved in 25–43 moles of methanol containing less than or equal to 5% water at 0–40° C. and diluting subsequently with water. The product was purified to have less than or equal to 20-ppm ionic impurities. The drawbacks of this process are that it uses corrosive bromine as brominating agent and half of the brominating agent ends-up as hydrobromic acid. Further, the reaction mixture has to be diluted extensively to obtain maximum TBBPA. As a result, the recovery of organic solvent and the byproduct hydrobromic acid from the filtrate to make the process cost benefit becomes quite expensive.

S. Armstrong U.S. Pat. No. 5,475,153, Cl. 568–726, C07 C39/367, Dec. 12, 1995 brominated the BPA with liquid bromine at 15–25° C. in $C_3$–$C_5$ alkanols and water to suppress the formation of alkyl bromides and then heated to 55–70° C. to get 98% pure TBBPA (mp, 180° C.). Hydrogen peroxide was combined with the reactants to reduce the amount of bromine required. The drawbacks of this are that it uses liquid bromine as brominating agent and requires a non-bromo compound, which decomposes spontaneously at room temperature to use the hydrobromic acid formed during the reaction.

DISCLOSURE OF THE INVENTION

The main object of the present invention is to provide a method of preparation of tetrabromobisphenol-A wherein the use of corrosive liquid bromine is eliminated and obviates the drawbacks as detailed above.

Another object of the present invention is to use the combination of bromide and bromate ions as brominating agent.

Yet, another object of the present invention is to use the aqueous mixtures of bromide and bromate salts obtained as intermediate in bromine manufacture.

Yet, another object of the present invention is to use bromate ion both as bromine source and as stable and non-contaminating oxidizing agent to achieve 100% bromine atom efficiency.

Yet, another object of the present invention is to use hydrobromic acid both as bromine source and as mineral acid to minimize requirement of additional acid in the reaction.

Still another object is to recycle the organic layer from the reaction mixture in subsequent batches to minimize processing time, maximize yield and minimize effluent discharge.

SUMMARY OF THE PRESENT INVENTION

The aim of present invention is to provide an eco-friendly method of preparation of a colorless tetrabromobisphenol-A with very good yields and maximum bromine efficiency. It has been surprisingly found that the 2:1 molar combination of bromate and bromide ions in the presence of a strong mineral acid rapidly produces-bromine which is completely utilized in the in situ bromination of bisphenol-A with minimum precautions and no special devices essential when liquid bromine is used. The present process is rapid, specific, environmental friendly and cost-effective giving high purity tetrabromobisphenol-A which melts at 180±2° C. The method gives 50–70% tetrabromobisphenol-A in first batch and 90–100% when the spent organic layer is recycled. The reaction takes 4–5 h. The isolated product obtained does not require no further recrystalization while the aqueous layer can be discharged safely. Such a compound is useful as a flame retardant and also in the preparation of acrylonitrile butadiene styrene polymer as well as in the epoxy and polycarbonate resins.

DESCRIPTION OF THE PRESENT INVENTION

Accordingly, the present invention provides an eco-friendly method of preparation of high purity tetrabromobisphenol-A through the bromination of bisphenol-A (BPA) with a combination of bromide and bromate ions by (a) dispersing 0.022–2.193 moles of bisphenol-A in 2 to 5 vol./wt of organic solvent and 3 to 8 times vol./wt of water, (b) reacting 0.059–5.855 moles of bromide salt of alkali or alkaline earth metal/hydrobromic acid and 0.030–2.939 moles of bromate as alkali/alkaline earth metal salt, (c) optionally adding 0.088–8.772 moles of 12 N hydrochloric acid in case of metal bromide or 0.030–2.939 equivalents in case of hydrobromic acid, (d) adding 0.01–0.5% wt/wt of alkyl sulfate salts having $C_6$–$C_{18}$ carbon chain is used as a surfactant at 5 to 45° C. over a period of 4 to 5 h under stirring, (d) separating the crystalline (50–70%) product; washing and drying of the product at 100° C., and (e) charging the organic layer containing un-reacted bisphenol-A, mono-, di- and tri-bromo derivatives and TBBPA with additional bisphenol-A and repeating the above process to yield 95–100% of TBBPA in the subsequent batches. In an embodiment of the present invention, the dispersing medium for bis phenol-A are organic solvents selected from methylene chloride and carbon tetrachloride or any other solvents.

In another embodiment of the present invention, the reactive brominating species such as elemental bromine and hydrobromite are generated in situ by the reaction of reacting 0.059–5.855 moles of alkali/alkaline earth metal bromide or hydrobromic acid with 0.030–2.939 moles of alkali/alkaline earth metal bromate, in the presence of 0.088–8.772 moles of hydrochloric acid, respectively.

In still another embodiment of the present invention, the bromination reaction is initiated by adding alkali/alkaline earth metal bromate dissolved in 3 (v/w) equivalent of water to bisphenol-A, alkali/alkaline earth metal bromide or hydrobromic acid, sodium lauryl sulfate and 12 N hydrochloric acid in methylene chloride or carbon tetra chloride.

In yet another embodiment of the present invention, the bromination reaction is initiated by adding the mixture of alkali/alkaline earth metal bromide and alkali/alkaline earth metal bromate dissolved in 3 (v/w) equivalents of water to bisphenol-A, sodium lauryl sulfate and 12 N hydrochloric acid in methylene chloride-water.

In yet another embodiment of the present invention, the bromination reaction is initiated by adding 12 N hydrochloric acid to bisphenol-A, alkali/alkaline earth metal bromide, alkali/alkaline metal bromate, sodium lauryl sulfate and 12 N hydrochloric acid in methylene chloride- water.

In yet another embodiment of the present invention, the bromination reaction is not affected by the change in the order of addition of the reagents used in the reaction.

In yet another embodiment of the present invention sodium bromide or 49%, wt/vol. hydrobromic acid dissolved in 3 to 8 (vol./wt) of de-ionized water is used as brominating agent.

In yet another embodiment of the present invention the ratio of organic solvents to Bis phenol A is maintained between 2:1 to 5:1.

In yet another embodiment of the present invention the ratio of organic solvents to Bis phenol A is maintained preferably between 3:1 to 5:1.

In yet another embodiment of the present invention the ratio of water: BPA is maintained between 3:1 to 8:1 to obtain shinny crystals of TBBPA.

In yet another embodiment of the present invention the ratio of water: BPA is maintained preferably between 5:1 to 8:1 to obtain shinny crystals of TBBPA.

In yet another embodiment of the present invention the reaction temperature is maintained between 5 to 45° C. to avoid loss of methylene chloride.

In yet another embodiment of the present invention the reaction temperature is preferably maintained between 10 to 15° C. to avoid loss of methylene chloride.

In yet another embodiment of the present invention use of hydrobromic acid minimizes the formation of by-product in the reaction.

In yet another embodiment of the present invention, the sodium bromate is used to act as both brominating and stable oxidizing agent.

In yet another embodiment of the present invention, 0.01 to 0.5% sodium lauryl sulfate is used as a surfactant for better dispersion.

In the conventional method of bromination, TBBPA is obtained from BPA and liquid bromine by the reaction depicted in equation 1.

$$BPA + 4\ Br_2 \rightarrow TBBPA + 4\ HBr \qquad (1)$$

According to the present invention, TBBPA is obtained via the overall reaction depicted in equation 2.

$$3\ BPA + 8\ Br^- + 4\ BrO_3^- + 12\ H^+ \rightarrow 3\ TBBPA + 12\ H_2O \qquad (2)$$

The stoichiometry of $BrO_3^-$ allows for oxidation of the added bromide and also hydrobromic acid produced during the bromination (eq 1). The reaction of bromate with bromide is depicted in equation 3.

$$5\ Br^- + BrO_3^- + 6\ H^+ \rightarrow 3\ Br_2 + 3\ H_2O \qquad (3)$$

If bromide and bromate ions are taken in the form of salts of sodium, The detailed stoichiometric equations for the overall bromination reactions with sodium bromide-sodium bromate and hydrobromic acid-sodium bromate are shown by equations 5 and 6, respectively wherein hydrochloric acid provides the required protons.

$$3\ BPA + 8\ NaBr + 4\ NaBrO_3 + 12\ HCl \rightarrow$$
$$3\ TBBPA + 12\ H_2O + 12\ NaCl \qquad (4)$$

$$3\ BPA + 8\ HBr + 4\ NaBrO_3 + 4\ HCl \rightarrow 3\ TBBPA + 12\ H_2O + 4\ NaCl \qquad (5)$$

These reactions were carried out in a round bottom (0.5 or 10.0 L) flask provided with the facility to add solutions slowly from outside and a mechanical device to stir the contents in it. A known quantity of BPA was suspended in methylene chloride or carbon tetrachloride-water mixture, with or without sodium lauryl sulfate as dispersing agent. Into this were added under stirring the calculated amounts of aqueous sodium bromide or hydrobromic acid and 12 N hydrochloric acid. The flask temperature was maintained in the range of 5–45° C. with cold water. The calculated amount of aqueous sodium bromate was added over 4–5 h under stirring. Stirring was continued for an additional 0.5 h. the contents were filtered. The fine crystals were washed with sufficient water, dried at 100° C., and weighed. The organic layer from the mother liquor was separated and evaporated to one-third of its original volume to get additional amount of crystalline TBBPA, which was filtered, washed with water, dried at 100° C., and weighed.

In another procedure, the organic layer at the end of the reaction was collected. After adjusting to its original volume, a fresh quantity of BPA was charged and the reaction repeated as above.

In a related procedure, the required quantities of the sodium salts of bromide and bromate in minimum quantity of water were taken along with the BPA-methylene chloride/carbon tetra chloride and the bromination reaction was initiated by the gradual addition of the required quantity of 12 N hydrochloric acid.

In another related procedure, the required quantity of 12 N hydrochloric acid was taken along with the BPA-methylene chloride/carbon tetrachloride and the bromination reaction initiated by the gradual addition of an aqueous solution containing the required quantities of sodium bromide and sodium bromate.

The methylene chloride/carbon tetra chloride: BPA (vol./wt) ratio was maintained between 2–5 in the reaction. It is advisable to maintain this ratio to 3 or above to avoid contamination of the TBBPA by the intermediates. On the other hand the water: BPA (vol./wt) was maintained between 3–8, more preferably in the ratio of 5–8 to obtain shining crystals of TBBPA.

The temperature of the vessel was controlled between 5–45° C. however, it is preferable to maintain the temperature between 10–15° C. to avoid the loss of methylene chloride.

The use of hydrobromic acid minimizes the requirement of additional mineral acid and also the formation of byproduct, salt in the reaction.

The purity as obtained with the product isolated in methylene chloride-water medium, was checked through elemental analysis, $^1$H-NMR and melting point and compared with theoretical carbon, hydrogen and bromine percentages of 33.08%, 2.20% and 58.8%, respectively, $^1$H-NMR (200 MHz) peaks in $MD_3OD$ as follows: 1.59 δ (s, 3H); 1.57 δ (s, 3H); 7.25 δ (s, 4H), and reported melting point of 181–182° C.

In the present invention, a colorless TBBPA is prepared in an environmental friendly manner with excellent yields in the range of 50–70% melting between 181–182° C., in the first batch and 90–100% melting between 178–182° C. in the subsequent batches when recycled the mother liquor. In this method, the use of toxic and corrosive bromine is avoided and sodium bromide or hydrobromic acid as brominating agent displaces it. Further the step of liberation of hydrobromic acid as byproduct is prevented. In addition, the methylene chloride-water or carbontetrachloride-water at 10–15° C. is used as the reaction medium. The minimum quantity of 12 N hydrochloric acid is used to assist the bromination reaction. The byproduct hydrobromic acid is utilized in the reaction to maintain the bromine atom efficiency maximum.

The important inventive steps involved in the present invention are (i) the use of liquid bromine as brominating is eliminated, (ii) the steps like heating and aging of the reactants after the addition of brominating agent which effect cost and production of TBBPA are eliminated, (iii) the pretreatment with sodium sulfite, aqueous hydrazine or recrystalization of the product are not essential, (iv) the present method of bromination of bisphenol-A does not require any special catalyst, (v) the methylene chloride or carbon tetrachloride and aqueous phase are immiscible and hence can easily be separated, (vi) the product TBBPA left after saturation in methylene chloride/carbon tetrachloride is obtained in pure form by simple filtration, (vii) the methylene chloride/carbon tetrachloride saturated with the product TBBPA can be reused in successive cycles to achieve maximum yields of TBBPA, (viii) the by-product sodium chloride released in the reaction, rapidly dissolves in aqueous solution and hence easily washable, (ix) the aqueous layer separated from the reaction vessel may be recycled or discharged safely after neutralizing the unutilized acid, (x) the brominating agent used in this method does not require any special skills and equipment and (xi) the oxidizing agent used in this method is a stable bromo compound and the bromine species released out of it also participate in the main reaction.

The present invention avoids the use of special equipment and devices, which are required for the handling of liquid bromine, hence economical. Further, the method reduces the cumbersome steps like recrystalization involved in obtaining high purity tetrabromobisphenol-A to meet the standards needed by the users. The method is also eco-friendly because it avoids the direct use of corrosive and fuming liquid bromine and minimizes the effluent discharge without the by-products like hydrobromic acid, alkyl bromides etc.

The following examples are given by way of illustrations and therefore should not be construed to limit the scope of the present invention.

EXAMPLE 1

To 25 g (0.11 moles) of bisphenol-A (BPA) in 75 ml of carbon tetrachloride in a two neck 500 ml round bottom flask, 31.62 g (0.31 moles or 2.80 equivalents) of sodium bromide and 0.05 g of sodium lauryl sulfate dissolved in 50 ml water and 45 ml (0.54 moles) of 12 N hydrochloric acid were added under stirring. The flask was cooled to 10° C. by placing it in a cold water bath. A solution of 22.1 g (0.15 moles or 1.34 equivalents) of sodium bromate in 75 ml water was slowly added over 4 h under stirring. The contents were stirred for another 30 min. The organic layer having fine colorless crystals of TBBPA at the bottom of flask was separated and concentrated to one-fourth of its volume. The product was filtered, washed twice with deionized water and dried in oven at 100° C. to give additional quantities of tetra bromo bisphenol-A. The total isolated yield of tetrabromo bisphenol-A was 92.28 %. The characteristic data recorded for the isolated sample were mp, 178–180° C.; $^1$H-NMR (CD$_3$OD, 200 MHz), 1.58 δ (s, 6H); 7.25 δ (s, 4H) in and elemental analysis, 33.21 (% C) 2.21 (% H) and 58.2 (% Br).

EXAMPLE 2

To 25 g (0.11 moles) of bisphenol-A in 75 ml of methylene chloride in a two neck 500 ml round bottom flask, 31.62 g (0.31 moles or 2.80 equivalents) of sodium bromide and 0.05 g of sodium lauryl sulfate dissolved in 50 ml water and 45 ml (0.54 moles) of 12 N hydrochloric acid were added under stirring. The flask was cooled to 10° C. by placing it in a cold water bath. A solution of 22.1 g (0.15 moles or 1.34 equivalents) of sodium bromate in 75 ml water was slowly added over 4 h under stirring The contents were stirred for another 30 min. The crystallized product was filtered, washed twice with deionized water and dried in oven at 100° C. to give 37.20 g (62.42% yield) of tetra bromo bisphenol-A (mp 181–182° C.) The organic layer was separated from the mother liquor and evaporated to one-fourth volume to obtain an additional 16.70 g of tetrabromo bisphenol-A (28.02% yield), bringing the total isolated yield of tetrabromo bisphenol-A to 90.44%. The characteristic data recorded for the isolated sample were mp, 181–182° C.; $^1$H-NMR (CD$_3$OD, 200 Mhz), 1.58 δ (s, 6H); 7.25 δ (s, 4H) and elemental analysis, 32.9 (% C), 2.19 (% H) and 58.3 (% Br).

EXAMPLE 3

To 25 g (0.11 moles) of bisphenol-A in 75 ml of methylene chloride in a two neck 500 ml round bottom flask, 31.62 g (0.31 moles or 2.80 equivalents) of sodium bromide and 0.05 g of sodium lauryl sulfate dissolved in 50 ml water and 45 ml (0.54 moles) of 12 N hydrochloric acid were added under stirring. The flask was cooled to 10° C. by placing it in a cold water bath. A solution of 22.1 g (0.15 moles or 1;34 equivalents) of sodium bromate in 75 ml water was slowly added over 4 h under stirring. The contents were stirred for another 30 min. The crystallized product was filtered, washed twice with deionized water and dried in oven at 100° C. to give 39.70 g (66.61% yield) of tetrabromo bisphenol-A (mp 181–182° C.). The organic layer (70-ml) was separated and re-used in the experiment of Example 4. The characteristic data recorded for the isolated sample were $^1$H-NMR (CD$_3$OD, 200 MHz), 1.58 δ (s, 6H); 7.25 δ (s, 4H) and elemental analysis, 32.9 (% C), 2.19 (% H) and 58.3 (% Br).

EXAMPLE 4

Into the organic layer obtained from the experiment of Example 3, 5 ml of methylene chloride was added to make up the volume to 75 ml. This was then taken in a two neck 500 ml round bottom flask and charged with fresh quantities of bisphenol-A, sodium bromide, hydrochloric acid, sodium lauryl sulfate and water in amount as mentioned in Example 3. The process of bromination described above was repeated by adding a solution of 22.1 g (0.15 moles or 1.34 equivalents) of sodium bromate in 75 ml water as in Example 3. After completion of the reaction, the product was filtered, washed and dried as in Example 3 to give 60.2 g or ca. 100% isolated yield of tetrabromo bisphenol-A (mp 181–182° C.) with respect to weight of the fresh charge of BPA. The organic layer was separated from the mother liquor and used in the experiment of Example 5. The characteristic data recorded for the isolated sample were $^1$H-NMR (CD$_3$OD, 200 MHz), 1.58 δ (s, 6H); 7.25 δ (s, 4H) and elemental analysis, 32.9 (% C), 2.19 (% H) and 58.3 (% Br).

EXAMPLE 5

The experiment as described in Example 4 was repeated using the spent organic layer from Example 4 after adjusting the volume to 75 ml with fresh methylene chloride. The isolated yield of tetrabromo bisphenol-A was 59.6 g or 100% with respect to the weight of fresh bisphenol-A charge and the melting point of the product was 180–182° C. No attempt was made to work up the organic layer. The characteristic data recorded for the isolated sample were $^1$H-NMR (CD$_3$OD, 200 MHz), 1.58 δ (s, 6H); 7.25 δ (s, 4H) and elemental analysis, 33.15 (% C), 2.18 (% H) and 57.8 (% Br).

EXAMPLE 6

To 25 g (0.11 moles) of bisphenol-A in 75 ml of methylene chloride in a two neck 500 ml round bottom flask, a solution of 31.62 g (0.31 moles or 2.80 equivalents) of sodium bromide and 22.1 g (0.15 moles or 1.34 equivalents) of sodium bromate containing 0.05 g of sodium lauryl sulfate dissolved in 110 ml of water was added. The flask was cooled to 10° C. by placing it in a cold water bath. To it, 45 ml (0.54 moles) of 12 N hydrochloric acid was added over 3 h under stirring. The contents were stirred for another half-an hour for completion of the reaction. The crystallized product was filtered, washed twice with deionized water and dried in oven at 100° C. to give 31.4 g (52.86% of tetrabromo bisphenol-A (mp 181–182° C.). The organic layer was recycled as described in Example 7. The characteristics data recorded for the isolated sample were $^1$H-NMR (CD$_3$OD, 200 MHz), 1.58 δ (s, 6H); 7.25 δ (s, 4H) and elemental analysis, 32.9 (% C), 2.19 (% H) and 58.3 (% Br).

EXAMPLE 7

The volume of the spent organic layer from the experiment of Example 6 was adjusted to 75 ml and the bromination was carried out by adding 25 gm.(0. 11 moles) of bisphenol-A , a solution of 31.62 gm. (0.31 moles or 2.80 equivalents) of sodium bromide and 22.1 gm. (0.15 moles or 1.34 equivalents) of sodium bromate containing 0.05 gm. of sodium lauryl sulfate dissolved in 110 ml. of water was added. The flask was cooled to 10° C. by placing it in a cold water bath. To it, 45 ml (0.54 moles) of 12 N Hydrochloric acid was added over 3 h under stirring. The solid product obtained was separated and the spent organic layer was reused in a successive batch. The weight of the total product obtained from the two successive batches was 121.90 g or ca. 100% with respect to the total bisphenol-A charge in the two batches. The melting point was 181–182° C. No attempt was made to either work-up or re-use the spent organic layer further. The characteristic data recorded for the isolated sample were $^1$H-NMR (CD$_3$OD, 200 MHz), 1.58 δ (s, 6H); 7.25 δ (s, 4H) and elemental analysis, 32.9 (% C), 2.19 (% H) and 58.3 (% Br).

EXAMPLE 8

To 0.50 kg (2.19 moles) of bisphenol-A in 1.50 1 of methylene chloride in a two neck 10 liter round bottom flask, a solution of 0.63 kg (6.14 moles) of sodium bromide, 0.44 kg (2.93 moles) of sodium bromate and 1 g of sodium lauryl sulfate in 2.5 1 of water was added. The flask was cooled to 10° C. by placing it in a cold water bath. To it, 0.90 1 (10.8 moles) of 12 N hydrochloric acid was added over 3 h under stirring. The contents were stirred for another 0.5 h and the separated solid product was filtered, washed twice with deionized water and dried in oven at 100° C. to give a yield of 0.85 kg. The organic layer was recycled with a fresh charge of 0.50 kg of bisphenol-A and other reagents as above and 1.07 kg of product was obtained. The organic layer was once again re-used in another batch to yield 1.14 kg of product. The isolated yield over three batches, ignoring residual product in the organic layer, was 85.4% while the melting point was 178–180° C. The characteristic data recorded for the isolated sample were $^1$H-NMR (CD$_3$OD, 200 MHz), 1.59 δ (s, 6H);

7.26 δ (s, 4H) and elemental analysis, 32.7 (% C), 2.15 (% H) and 57.3 (% Br).

EXAMPLE 9

To 25 g (0.11 moles) of bisphenol-A in 75 ml of methylene chloride in a two neck 500 ml round bottom flask, 0.31 moles (37.5 ml of 49% w/w) of hydrobromic acid, 0.05 g of sodium lauryl sulfate and 9 ml (0.11 moles) of 12 N hydrochloric acid were added under stirring. The flask was cooled to 10° C. by placing it in a cold water bath. A solution of 22.1 g (0.15 moles or 1.34 equivalents) of sodium bromate in 75 ml water was slowly added over 4.25 h under stirring. The contents were stirred for another 30 min. The solid product obtained (32.30 g) was collected and an additional quantity of product (22.60 g) was recovered from the organic layer as described in Example 2. The combined product was filtered, washed twice with deionized water and dried in oven at 100° C. to give a total of 92.11% yield of TBBPA (mp 181–182° C.). The characteristic data recorded for the isolated sample were $^1$H-NMR (CD$_3$OD, 200 MHz), 1.58 δ (s, 6H); 7.25 δ (s, 4H) and element analysis, 32.9 (% C), 2.19 (% H) and 58.3 (% Br).

EXAMPLE 10

25 g (0.11 moles) of bisphenol-A was stirred in 75 ml of methylene chloride taken in a two-neck 500 ml round bottom flask. The flask was cooled to 10° C. by placing it in a cold water bath. To it, 45 ml (0.54 moles) of 12 N hydrochloric acid and 0.05 g of sodium lauryl sulfate were added under stirring. A solution containing 31.62 g (0.31 moles or 2.80 equivalents) of sodium bromide and 22.10 g (0.15 moles or 0.34 equivalents) of sodium bromate in 110 ml of water was added over 4 h under stirring. The stirring was continued for another 0.5 h, the solid product obtained was collected and an additional quantity of product was recovered from the organic layer to give an overall yield of 93% of tetrabromo bisphenol-A (mp 181–182° C.). The characteristic data recorded for the isolated sample were $^1$H-NMR (CD$_3$OD, 200 MHz), 1.58 δ (s, 6H); 7.25 δ (s, 4H) and elemental analysis, 32.9 (% C), 2.19 (% H) and 58.3 (% Br).

The experimental data revealed that Tetrabromobisphenol-A (TBBPA) could be prepared in good yields and with high bromine atom efficiency by a safe, simple and economical method as alternative to those involving liquid bromine as brominating agent and considerable degree of work-up to recover product. The present method is more advantageous because the handling of brominating agents and other reactants is much easier than those in other methods. It does not require any special catalyst, which can add impurities to the product, and it does not depend on extraneous oxidizing agents to use the hydrobromic acid by-product generated in the course of the bromination reaction. The method of the invention allows flexibility in the bromide- and bromate-containing compounds used and in the manner of addition of reagents which, in turn, is suited to the use of bromide-bromate mixture generated as intermediate in the recovery of bromine by the cold process. Further, the bromination reaction is carried out near-ambient condition and pure product is obtained directly in solid form thereby minimizing the requirement for work-up and purification. The method of the invention also envisages re-use of the spent organic layer in successive batches and thus simultaneously achieves the advantages of maximum product recovery and minimum organic effluent discharge.

THE MAIN ADVANTAGES OF THIS METHOD ARE

1. It does not use directly liquid bromine for bromination of BPA.

2. The brominating agents and other reactants are eco-friendly but not toxic and air pollutants.

3. The brominating agents do not require special equipment and safety devices.

4. It does not require any catalyst and thus polycarbonate grade TBBPA can be obtained directly.

5. Side products like hydrobromic acid are not produced.

6. The oxidizing agent used in this method for the oxidation of hydrobromic acid is stable and the product released from this adds to the active brominating species.

7. It does not require to heat or store the reaction mixture after the complete addition of brominating agent.

8. The alkaline solution obtained as the intermediate in the process of bromine extraction from bittern by cold process can be used as brominating agent.

9. The mineral acid, hydrochloric acid is not as hazardous as others and its quantity can be minimized.

10. The bromination reaction is carried out at near-ambient condition and pure product is obtained directly in solid form thereby minimizing the requirement for work-protocol and purification.

11. The spent organic layer can be recycled in successive batches and thus simultaneously achieves the advantages of maximum product recovery and minimum organic effluent discharge.

12. The organic layer and the aqueous layer separated from the mother liquor can be reused without the necessity of any pretreatment.

13. The product can be obtained directly as a crystalline material in pure form in 5 to 7 h after starting the reaction.

14. The organic layer can be recycled in subsequent batches to minimize work-protocol, obtain maximum yield of readily insoluble product and to minimize effluent discharge.

What is claimed is:

1. A method for the preparation of tetrabromobisphenol-A (TBBPA) through the bromination of bisphenol-A(BPA) with a combination of bromide and bromate ions, which comprises the steps of:
   (a) dispersing 0.022 to 2.193 moles of bisphenol-A in 2 to 5 ml/g of organic solvents and 3 to 8 times ml/g of water,
   (b) reacting 0.059 to 5.855 moles of a bromide salt of an alkali or alkaline earth metal or hydrobromic acid and 0.030 to 2.939 moles of a bromate as an alkali or alkaline earth metal salt,
   (c) optionally adding 0.088 to 8.772 moles of 12 N hydrochloric acid in case of metal bromide or 0.030 to 2.939 equivalents in case of hydrobromic acid,
   (d) adding 0.01 to 0.5% wt/wt of an alkyl sulfate salt surfactant having a $C_6$–$C_{18}$ carbon chain at 5 to 45° C. over a period of 4 to 5 hrs under stirring,
   (e) separating the crystalline product in 50 to 70% yield; washing and drying the product at 100° C., and
   (f) charging the organic layer containing unreacted bisphenol-A, mono-, di- and tri-bromo derivatives and TBBPA with additional bisphenol-A and repeating the above process to yield 95 to 100% of TBBPA in the subsequent batches.

2. A method as claimed in claim 1 wherein, the organic solvents used independently to disperse BPA are methylene chloride and carbon tetrachloride.

3. The method as claimed in claim 1, wherein the bromination reaction is initiated by adding the alkali or the alkaline earth metal bromate dissolved in 3 (ml/g) equivalents of water to bisphenol-A, alkali or alkaline earth metal bromide or hydrobromic acid, sodium lauryl sulfate and 12 N hydrochloric acid in methylene chloride or carbon tetra chloride.

4. The method as claimed in claim 1, wherein the bromination reaction is initiated by adding a mixture of alkali or alkaline earth metal bromide and alkali or alkaline earth metal bromate dissolved in 3 (ml/g) equivalents of water to bisphenol-A, sodium lauryl sulfate and 12 N hydrochloric acid in methylene chloride-water.

5. The method as claimed in claim 1, wherein the bromination reaction is initiated by adding 12 N hydrochloric acid to bisphenol-A, alkali or alkaline earth metal bromide, alkali or alkaline earth metal bromate, sodium lauryl sulfate and 12 N hydrochloric acid in methylene chloride-water.

6. The method as claimed in claim 1, wherein the addition of reactants during bromination may occur in any sequence.

7. The method as claimed in claim 1, wherein the ratio of organic solvents to bisphenol-A is maintained between 3:1 to 5:1.

8. The method as claimed in claim 1, wherein the ratio of water: BPA is maintained between 5:1 to 8:1.

9. A method as claimed in claim 1 wherein, the reaction temperature is maintained between 5 to 45° C. to avoid loss of methylene chloride.

10. The method as claimed in claim 1, wherein the reaction temperature is maintained between 10 to 15° C.

11. The method as claimed in claim 1, wherein the hydrobromic acid used is converted to bromine to minimize by-product formation.

12. The method as claimed in claim 1, wherein sodium bromide or 49% mg/ml hydrobromic acid is used to facilitate the bromination reaction.

13. The method as claimed in claim 1, wherein the bromate is sodium bromate.

14. The method as claimed in claim 1, wherein the surfactant is sodium lauryl sulfate.

15. A method as claimed in claim 1 wherein, the product TBBPA obtained from the reaction is having the following characteristics.
   i) melting range 178–182° C.,
   ii) 1H-NMR peaks 1.57 δ (s, 3H), 1.59 δ (s, 3H) and 7.25 δ (s, 3H), and
   iii) elemental analysis range % C, 33.00–33.22; % H 2.18–2.21; and % Br 58.00–58.68.

* * * * *